United States Patent [19]

Franke, deceased et al.

[11] Patent Number: 4,670,435

[45] Date of Patent: Jun. 2, 1987

[54] 10,11-DIHYDRO-5H-DIBENZO[A,D]CYCLOHEPTADIENE DERIVATIVES IN A METHOD FOR TREATING CARDIAC ARRHYTHMIA

[75] Inventors: Albrecht Franke, deceased, late of Wachenheim, Fed. Rep. of Germany, Renate Elisabeth Franke nee ée Alm, Catharina Franke, Tobias Franke, heirs; Claus D. Mueller, Viernheim; Dieter Lenke, Ludwigshafen, both of Fed. Rep. of Germany

[73] Assignee: BASF Aktiengesellschaft, Fed. Rep. of Germany

[21] Appl. No.: 803,576

[22] Filed: Dec. 2, 1985

[30] Foreign Application Priority Data

Dec. 8, 1984 [DE]  Fed. Rep. of Germany ....... 3444837

[51] Int. Cl.[4] ................. A61K 31/135; A61K 31/445; A61K 31/535
[52] U.S. Cl. ..................................... 514/239; 514/325; 514/653; 564/337; 564/355; 544/154; 546/203
[58] Field of Search ........................ 544/154; 546/203; 564/319, 355, 337; 514/239, 325, 653

[56] References Cited

U.S. PATENT DOCUMENTS 3,215,739  11/1965  Holm ................................... 564/355

FOREIGN PATENT DOCUMENTS 2323758  1/1983  Fed. Rep. of Germany .
2043457  2/1971  France .

OTHER PUBLICATIONS

Burger, *Medicinal Chemistry*, 4th ed., part 111, pp. 481, 482, 574, 575, 900–902, 1000, 1001, 1022–1027.

*Primary Examiner*—Robert W. Ramsuer
*Attorney, Agent, or Firm*—Keil & Weinkauf

[57] ABSTRACT

10,11-Dihydro-5H-dibenzo[a,d]cycloheptadiene derivatives of the formula I

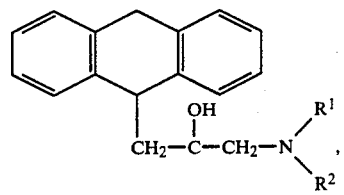

where $R^1$ and $R^2$ have the meanings stated in the description, and their preparation are described. The novel substances are useful for the treatment of disorders.

1 Claim, No Drawings

10,11-DIHYDRO-5H-DIBENZO[A,D]CYCLOHEPTADIENE DERIVATIVES IN A METHOD FOR TREATING CARDIAC ARRHYTHMIA

The present invention relates to novel 10,11-dihydro-5H-dibenzo[a,d]cycloheptadiene derivatives, a process for their preparation and their use in the treatment of disorders.

German Laid-Open Application No. DOS 2,328,758 discloses diphenylmethyl derivatives of the formula $(C_6H_5)_2CH-CH_2-COH(CH_3)-CH_2-NH-$alkyl which act on the central nervous system and have a spasmolytic action as well as an antiarrhythmic action.

We have found that 10,11-dihydro-5H-dibenzo[a,d]cycloheptadiene derivatives of the formula I

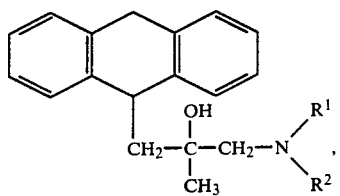

I where $R^1$ is hydrogen, $C_1$-$C_6$-alkyl, $C_2$-$C_6$-alkenyl, $C_2$-$C_6$-alkynyl, $C_1$-$C_6$-hydroxyalkyl or $C_1$-$C_4$-alkoxy-$C_1$-$C_4$-alkyl and $R_2$ is hydrogen, or $R^1$ and $R^2$, together with the nitrogen atom which connects them to one another, form a morpholine ring or a piperidine ring which may be substituted in the 4-position by hydroxyl and/or by unsubstituted or halogen-substituted phenyl, and their salts with physiologically tolerated acids are useful for the therapy of arrhythmias.

Preferred acids for the formation of physiologically tolerated salts are hydrohalic acids, such as hydrobromic acid and in particular hydrochloric acid, with which the novel compounds form salts which crystallize particularly readily. Other examples are phosphoric acid, nitric acid, sulfuric acid, monofunctional and bifunctional carboxylic acids and hydroxycarboxylic acids, such as acetic acid, oxalic acid, maleic acid, succinic acid, fumaric acid, tartaric acid, citric acid, salicylic acid, sorbic acid or lactic acid, and sulfonic acids, such as p-toluenesulfonic acid and naphthalene-1,5-disulfonic acid.

The novel compounds can be prepared by a method in which 2-[(10,11-dihydro-5H-dibenzocycloheptadienyl)methyl]-2-methyloxirane is reacted with an amine of the formula $HNR^1R^2$, where $R^1$ and $R^2$ have the stated meanings, and, if required, the resulting compound is converted to its salts with physiologically tolerated acids.

As a rule, the solvent used is a lower alcohol, preferably ethanol or n-propanol, and the reaction is advantageously carried out at the boiling point of the alcohol used. However, it is also possible to use other solvents, such as tetrahydrofuran, dioxane, acetonitrile or dimethylformamide.

When the reaction is complete, the compound obtained is advantageously purified by distillation, or by conversion to an addition salt with an acid followed by recrystallization.

The 2-[(10,11-dihydro-5H-dibenzocycloheptadienyl)-methyl]-2-methyloxirane required for the preparation of the novel substances can be obtained by reacting (10,11-dihydro-5H-dibenzocycloheptadienyl)-acetone with trimethylsulfoxonium iodide in the presence of sodium hydroxide in dimethyl sulfoxide (cf. J. Amer. Chem. Soc. 84, (1962) 3782).

The preparation gives the novel compounds in the form of racemates, which, if desired, can be separated into the optical antipodes by fractional crystallization of suitable salts of optically active acids by a conventional method.

The compounds according to the invention and their physiologically tolerated addition salts with acids possess antiarrhythmic properties and are therefore particularly useful for the treatment of cardiac arrhythmias, for the prophylaxis of sudden heart death and for the treatment of coronary heart disease. To investigate the pharmacodynamic properties of the novel products, the following method was used:

The substances were administered orally to Sprague-Dawley rats weighing 200–250 g. 45 minutes thereafter, the animals were anesthetized with 100 mg/kg of thiobutabarbital Na, administered intraperitoneally. Aconitine, as an arrhythmogenic substance, was infused intravenously into the jugular vein 60 minutes after administration of the substance (dosage rate: 0.005 mg per kg per min). In the case of untreated animals (N=52), arrhythmias appeared in the ECG after 2.74±0.07 minutes, the appearance of these arrhythmias being delayed by antiarrhythmic agents in a dose-dependent manner.

The dose which prolongs the duration of aconitine infusion by 50%, ie. the ED 50%, was determined from the linear relationship between log dose (mg/kg) of the test substances and the relative prolongation of aconitine infusion duration ($\Delta\%$).

Furthermore, the dose at which toxic symptoms (change in the initial ECG, cyanosis or cramp) occur was determined from the geometric progression of doses (factor 2.154) used in the experiments.

The quotient of acute toxic dose to antiarrhythmic ED 50% was determined as a measure of the therapeutic index of the novel compounds.

The novel compounds have an antiarrhythmic action when administered orally in doses of less than 43.5 mg/kg and are therefore clearly superior to the comparative substance quinidine. They also possess a greater therapeutic index than the comparative compound.

TABLE 1

| | Antiarrhythmic action Rat, oral administration |
|---|---|
| Example | ED 50% (mg/kg)[1] |
| 1 | 6.51 |
| 9 | 2.57 |
| 3 | 3.11 |
| 4 | 6.47 |
| 6 | 6.83 |
| 5 | 7.78 |
| Quinidine | 43.5 |

[1]Dose (mg/kg) which prolongs the aconitine infusion duration by 50%.

TABLE 2

| | Antiarrhythmic action and toxicity Rat, oral administration | | |
|---|---|---|---|
| Example No. | ED 50%[1] (mg/kg) | Toxic dose (mg/kg[2]) | Q[3] |
| 3 | 3.11 | 100 | 32 |
| 4 | 6.47 | 215 | 33 |

TABLE 2-continued

| | Antiarrhythmic action and toxicity Rat. oral administration | | |
|---|---|---|---|
| Example No. | ED 50%[1] (mg/kg) | Toxic dose (mg/kg[2]) | Q[3] |
| Quinidine | 43.5 | 464 | 11 |

[1]Dose which prolongs the aconitine infusion duration by 50%.
[2]Dose (mg/kg) at which the first toxic symptoms are observed.
[3]$Q = \frac{\text{Toxic dose}}{\text{ED 50\%}}$ The novel compounds can be administered orally or parenterally (intravenously, intramuscularly) in a conventional manner.

The dosage depends on the age, condition and weight of the patient and on the route of administration. As a rule, the daily dose of active compound is from about 0.5 to 15 mg/kg of body weight in the case of oral administration and from about 0.005 to 0.1 mg/kg of body weight in the case of parenteral administration.

The novel compounds may be employed in the conventional solid or liquid pharmaceutical forms, such as tablets, film tablets, capsules, powders, granules, coated tablets, suppositories or solutions. These are prepared in a conventional manner, and to do so the active compounds can be mixed with the conventional pharmaceutical auxiliaries, such as tablet binders, fillers, preservatives, tablet disintegrating agents, flow regulators, plasticizers, wetting agents, dispersants, emulsifiers, solvents, retarding agents, antioxidants and/or propellants (cf. H. Sucker et al., Pharmazeutische Technologie, Thieme-Verlag, Stuttgart, 1978). The administration forms thus obtained normally contain from 0.1 to 99% by weight of the active compound.

The Examples which follow illustrate the invention.

A.

Preparation of the starting compound 4 g (0.133 mole) of sodium hydride (80% strength in liquid paraffin) are suspended in 175 ml of anhydrous dimethyl sulfoxide, and 28.5 g (0.133 mole) of trimethyl sulfoxonium iodide are added a little at a time, at from 15° to 20° C., to the stirred and cooled suspension. When evolution of hydrogen is complete, cooling is discontinued and 25 g (0.1 mole) of (10,11-dihydro-5H-dibenzocycloheptadienyl)-acetone, dissolved in 80 ml of anhydrous dimethyl sulfoxide, are introduced in the course of 1 hour, after which stirring is continued for a further 2 hours at 40° C. The reaction solution is poured onto 2 l of ice water, stirred for 2 hours, while cooling, and then extracted with diethyl ether, and the extracting agent is distilled off.

25.9 g of 2-[10,11-dihydro-5H-dibenzocycloheptadienyl)-methyl]-2-methyloxirane are isolated as a crude product, which can be used without further purification.

B.

Preparation of the end products

Example 1

7 g (0.027 mole) of 2-[10,11-dihydro-5H-dibenzocycloheptadienyl)-methyl]-2-methyloxirane and 4 ml of isopropylamine in 50 ml of isopropanol are refluxed for 8 hours.

The solvent is distilled off under reduced pressure, the residue is taken up in ether, the ether solution is washed with water and then dried with $Na_2SO_4$, and HCl gas is passed in until the solution gives a neutral reaction. The precipitate formed is filtered off and recrystallized from acetone/ether.

3.6 g (37%) of N-[2-hydroxy-2-methyl-3-(10,11-dihydro-5H-dibenzocycloheptadienyl)-propyl]-N-isopropylamine hydrochloride of melting point 158° C. are isolated in this manner.

The compounds below were prepared, or can be prepared, by a similar method.

| Example | $R^1$ | $R^2$ | mp. [°C.] hydrochloride |
|---|---|---|---|
| 2 | —H | H | 192 |
| 3 | —$CH_3$ | H | 207 |
| 4 | —$C(CH_3)_3$ | H | 211 |
| 5 | —$CH_2$—$CH_2$—$CH_3$ | H | 169 |
| 6 | —$C(CH_3)$—$CH_2OCH_3$ | H | 136 |
| 7 | —$(CH_2)_5$— | | 195 |
| 8 | —$(CH_2)_2$—O—$(CH_2)_2$— | | 157 |
| 9 | —$CH_2$—$CH_2$—C(OH)($C_6H_5$)—$CH_2$—$CH_2$— | | 161 |
| 10 | —$C(CH_3)_2$—C≡CH | H | 232 |
| 11 | —$CH_2$—$CH_3$ | H | |
| 12 | —$CH_2$—$(CH_2)_2$—$CH_3$ | H | |
| 13 | —$CH_2$—$CH(CH_3)$—$CH_3$ | H | |
| 14 | —$CH_2$—$(CH_2)_4$—$CH_3$ | H | |
| 15 | —$CH_2$—$CH(CH_3)$—$(CH_2)_2$—$CH_3$ | H | |
| 16 | —$CH_2$—C≡CH | H | |
| 17 | —$CH(CH_3)$—C≡CH | H | |
| 18 | —$CH_2$—$CH_2OH$ | H | |

We claim:

1. The method of treating cardiac arrhythmias in a patient suffering therefrom which comprises administering to the patient an effective amount of a 10,11-dihydro-5H-dibenzo[a,d]cycloheptadiene derivative of the formula I

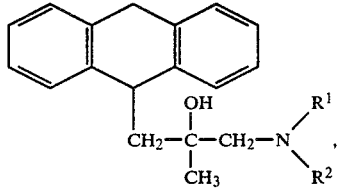

where $R^1$ is hydrogen, $C_1$–$C_6$alkyl, $C_2$–$C_6$alkenyl, $C_2$–$C_6$-alkynyl, $C_1$–$C_6$-hydroxyalkyl or $C_1$–$C_4$-alkoxy-$C_1$–$C_4$-alkyl and $R^2$ is hydrogen, or $R^1$ and $R^2$, together with the nitrogen atom which connects them to one another, form a morpholine ring or a piperidine ring which may be substituted in the 4-position by hydroxyl and/or by unsubstituted or halogen-substituted phenyl, and its salts with physiologically tolerated acids.

* * * * *